(12) United States Patent
Keil et al.

(10) Patent No.: US 12,036,417 B2
(45) Date of Patent: Jul. 16, 2024

(54) HIGH VOLTAGE THERAPY SYSTEM WITH TRANSFORMER PRIMARY CURRENT CONTROL

(71) Applicant: CARDIAC PACEMAKERS, INC., St. Paul, MN (US)

(72) Inventors: Brandon Tyler Keil, Maple Grove, MN (US); William J. Linder, Golden Valley, MN (US); Keith R. Maile, New Brighton, MN (US)

(73) Assignee: CARDIAC PACEMAKERS, INC.

(*) Notice: Subject to any disclaimer, the term of this patent is extended or adjusted under 35 U.S.C. 154(b) by 695 days.

(21) Appl. No.: 17/174,891

(22) Filed: Feb. 12, 2021

(65) Prior Publication Data

US 2021/0257849 A1 Aug. 19, 2021

Related U.S. Application Data

(60) Provisional application No. 62/976,137, filed on Feb. 13, 2020.

(51) Int. Cl.
| | |
|---|---|
| *A61N 1/39* | (2006.01) |
| *A61N 1/378* | (2006.01) |
| *H02J 7/00* | (2006.01) |
| *H02J 50/10* | (2016.01) |
| *H02J 7/02* | (2016.01) |

(52) U.S. Cl.
CPC ......... *A61N 1/39622* (2017.08); *A61N 1/378* (2013.01); *A61N 1/3782* (2013.01); *A61N 1/3981* (2013.01); *H02J 7/00714* (2020.01); *H02J 50/10* (2016.02); *H02J 7/02* (2013.01)

(58) Field of Classification Search
None
See application file for complete search history.

(56) References Cited

U.S. PATENT DOCUMENTS

| | | | |
|---|---|---|---|
| 5,507,781 A | 4/1996 | Kroll et al. | |
| 5,643,323 A | 7/1997 | Kroll et al. | |
| 6,208,895 B1* | 3/2001 | Sullivan | A61N 1/3904 607/4 |
| 6,647,292 B1 | 11/2003 | Bardy et al. | |

(Continued)

OTHER PUBLICATIONS

Steven Keeping, "The Advantages of Pulse Frequency Modulation for DC/DC Switching Voltage Converters," Mar. 25, 2014, Electronic Products Magazine. https://www.digikey.com/en/articles/the-advantages-of-pulse-frequency-modulation-for-dc-dc-switching-voltage-converters (Year: 2014).*

*Primary Examiner* — Michael W Kahelin
*Assistant Examiner* — Luke M Stanley
(74) *Attorney, Agent, or Firm* — Seager, Tufte & Wickhem LLP (57) ABSTRACT

Improved devices, circuits and methods of operation in implantable stimulus systems. An implantable defibrillator may comprise a charging circuit using a transformer to store and build up energy on an HV capacitor or capacitor stack, with the HV capacitor in turn coupled to an H-bridge output circuit having low and high sides for issuing therapy. A current monitoring circuitry is provided on the low side of the H-Bridge and used to form a feedback loop to control current into a transformer that converts battery voltage to a signal that charges the HV capacitor to control current through the H-bridge.

10 Claims, 6 Drawing Sheets

(56) References Cited

U.S. PATENT DOCUMENTS

| | | |
|---|---|---|
| 6,721,597 B1 | 4/2004 | Bardy et al. |
| 6,754,528 B2 | 6/2004 | Bardy et al. |
| 6,778,860 B2 | 8/2004 | Ostroff et al. |
| 6,865,417 B2 | 3/2005 | Rissmann et al. |
| 6,952,608 B2 | 10/2005 | Ostroff |
| 6,954,670 B2 | 10/2005 | Ostroff |
| 6,968,231 B1 | 11/2005 | Silvian et al. |
| 7,149,575 B2 | 12/2006 | Ostroff et al. |
| 7,330,757 B2 | 2/2008 | Ostroff et al. |
| 7,555,338 B2 | 6/2009 | Ostroff |
| 7,783,340 B2 | 8/2010 | Sanghera et al. |
| 7,860,565 B2 | 12/2010 | Brink |
| 7,877,139 B2 | 1/2011 | Ostroff |
| 8,157,813 B2 | 4/2012 | Ko et al. |
| 8,160,686 B2 | 4/2012 | Allavatam et al. |
| 8,200,341 B2 | 6/2012 | Sanghera et al. |
| 8,209,005 B1 | 6/2012 | Moulder et al. |
| 8,463,392 B2 | 6/2013 | Aghassian |
| 8,473,066 B2 | 6/2013 | Aghassian et al. |
| 8,532,785 B1 | 9/2013 | Crutchfield et al. |
| 8,548,590 B2 | 10/2013 | Aghassian |
| 8,565,878 B2 | 10/2013 | Allavatam et al. |
| 8,825,157 B2 | 9/2014 | Warren et al. |
| 8,972,005 B2 | 3/2015 | Rasmussen et al. |
| 8,983,599 B2 | 3/2015 | Garrett et al. |
| 9,579,517 B2 | 2/2017 | Meador et al. |
| 9,641,012 B2 | 5/2017 | Cabelka et al. |
| 9,643,025 B2 | 5/2017 | Crutchfield et al. |
| 9,750,950 B2 | 9/2017 | Norton et al. |
| 9,814,889 B2 | 11/2017 | Strommer et al. |
| 9,861,827 B2 | 1/2018 | Cabelka et al. |
| 9,861,828 B2 | 1/2018 | Norton et al. |
| 9,956,442 B2 | 5/2018 | Cooper et al. |
| 10,046,168 B2 | 8/2018 | Nikolski et al. |
| 10,050,700 B2 | 8/2018 | Ludwig et al. |
| 10,080,905 B2 | 9/2018 | Anderson et al. |
| 10,155,119 B2 | 12/2018 | Anderson et al. |
| 10,159,847 B2 | 12/2018 | Rasmussen et al. |
| 10,213,610 B2 | 2/2019 | Maile et al. |
| 10,350,425 B2 | 7/2019 | Nikolski et al. |
| 10,471,267 B2 | 11/2019 | Thompson-Nauman et al. |
| 10,556,118 B2 | 2/2020 | Anderson et al. |
| 2006/0167503 A1 | 7/2006 | Warren et al. |
| 2006/0241698 A1* | 10/2006 | Ostroff ............... A61N 1/3937 607/2 |
| 2008/0065160 A1* | 3/2008 | Brink ................. A61N 1/3625 607/4 |
| 2012/0029335 A1 | 2/2012 | Sudam et al. |
| 2016/0067509 A1* | 3/2016 | Meador ............... A61N 1/3956 607/5 |
| 2017/0021159 A1 | 1/2017 | Reddy et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2018/0036527 A1 | 2/2018 | Reddy et al. |
| 2018/0036547 A1 | 2/2018 | Reddy |
| 2018/0133462 A1 | 5/2018 | Reddy |
| 2021/0252296 A1 | 8/2021 | Keil et al. |
| 2021/0252299 A1 | 8/2021 | Keil et al. |
| 2021/0283409 A1 | 9/2021 | Keil et al. |

* cited by examiner

HIGH VOLTAGE THERAPY SYSTEM WITH TRANSFORMER PRIMARY CURRENT CONTROL

CROSS REFERENCE TO RELATED APPLICATIONS

This application claims the benefit of and priority to U.S. Provisional Patent Application Ser. No. 62/976,137 filed on Feb. 13, 2020, the disclosure of which is incorporated herein by reference.

BACKGROUND

Battery powered implantable devices, such as implantable defibrillators, may generate output stimuli having a larger voltage than the batteries of such devices can directly provide. Voltage boosting circuitry is typically used to create the higher voltages, including, for example, switched capacitor and/or transformer-based DC:DC conversion circuitry. In an implantable defibrillator, for example, a DC:DC circuit, such as a flyback transformer circuit, can be used to transfer power from a battery to a high power capacitor stack until the energy stored on the capacitor stack meets a therapy threshold. The stored energy is then discharged to the patient.

When discharging energy to the patient, it is common to deliver therapy in a biphasic pattern that requires switching the direction of current flow. An H-Bridge circuit is often used to provide the switching capability. The switches of an H-Bridge, which may take the form of junction or field effect transistors, silicon controlled rectifiers, or other suitable circuitry, may be used in an ON/OFF manner, in which currents are not controlled, for delivering high power therapy such as defibrillation. It may be desirable in some instances to reuse this circuitry to provide controlled current outputs. New and alternative circuit designs and methods for providing controlled current outputs are desired.

OVERVIEW

The present inventors have recognized, among other things, that a problem to be solved is the need for new and/or alternative circuit designs for using and reusing defibrillation output circuitry to deliver controlled current pacing or induction pulses.

A first illustrative, non-limiting example takes the form of an electronic circuit for controlling an output of an implantable medical device, the electronic circuit comprising: a transformer having a primary winding and at least one secondary winding; a power source selectively electrically coupled to the primary winding; a load coupled to the at least one secondary winding; a current sensing subcircuit coupled to the load; a charge control circuit configured to enable and disable current through the primary winding, wherein the charge control circuit takes a feedback signal from the current sensing subcircuit to control current through the primary winding, thereby controlling current output to the load via selective enabling and disabling of the power source to the primary winding.

Additionally or alternatively, the load comprises at least first and second capacitors each independently coupled to a secondary winding.

Additionally or alternatively, the charge control circuit is operable in a current controlling mode and defibrillation mode, wherein the current controlling mode is one in which the charge control circuit uses the feedback signal, and in the defibrillation mode, the charge control circuit does not use the feedback signal, to enable and disable current through the primary winding.

Additionally or alternatively, the charge control circuit comprises a control subcircuit that issues charger enable pulses to a switch in series with the primary winding to thereby transfer energy from the battery to the transformer, wherein the charge control subcircuit is configured to modulate characteristics of the charger enable pulses in response to the feedback signal.

Additionally or alternatively, the charge control subcircuit is configured to adjust a width of one or more charger enable pulses. Additionally or alternatively, the charge control subcircuit is configured to adjust a period between successive ones of the charger enable pulses. Additionally or alternatively, the charge control subcircuit is configured to issue the charger enable pulses as a series of bursts of charger enable pulses, and, to modulate characteristics of the charger enable pulses, the charge control subcircuit is configured to omit at least one burst of the series of bursts. Additionally or alternatively, the charge control subcircuit is configured to issue the charger enable pulses as a series of bursts of charger enable pulses, and, to modulate characteristics of the charger enable pulses, the charge control subcircuit is configured to change how many pulses are in each of the series of bursts.

Another illustrative, non-limiting example takes the form of an implantable pacemaker-defibrillator comprising the electronic circuit of the first illustrative, non-limiting example, wherein the power source takes the form of a battery, and the load comprises: a capacitor circuit coupled to the at least one secondary winding; an H-bridge to deliver electrical signals from the capacitor stack to outputs of the defibrillator; a system controller for the implantable defibrillator having control outputs to control operation of the H-Bridge and the charge control circuit; and a housing containing the battery, transformer, capacitor stack, H-bridge, current sensing subcircuit, charge control circuit and system controller; wherein the system controller is configured to selectively operate the charge control circuit in a pacing mode in which a feedback signal from the current sensing subcircuit is used to control current through the primary winding by operation of the charge control circuit.

Additionally or alternatively, the implantable pacemaker-defibrillator may comprise a lead having a distal end comprising a therapy delivery electrode, a proximal end with a plug having at least a first electrical connector, and lead body connecting the proximal and distal ends with at least one conductor therein coupling the first electrical connector to the therapy delivery electrode, wherein the housing includes a port for coupling to the lead, the port including a second electrical connector for coupling to a corresponding electrical connector of the lead, and the H-bridge is electrically coupled to the second electrical connector.

Additionally or alternatively, the system controller is configured to selectively operate the charge control circuit in a defibrillation mode in which the current sensing subcircuit is bypassed.

Additionally or alternatively, the system controller is configured to selectively operate the charge control circuit in an induction mode in which the feedback signal from the current sensing subcircuit is used to control current through the primary winding by operation of the charge control circuit.

Additionally or alternatively, the capacitor circuit comprises a plurality of capacitors each coupled to a secondary winding of the transformer, respectively, and dischargeable in series through the H-Bridge.

A third illustrative, non-limiting example takes the form of a method of operation in an implantable medical device comprising a transformer having a primary winding and at least one secondary winding, a power source selectively electrically coupled to the primary winding, a load coupled to the at least one secondary winding, a current sensing subcircuit coupled to the load, and a charge control circuit configured to enable and disable current through the primary winding, the method comprising: using the charge control circuit to cause the transformer to transfer electrical signal from the power source to the load; monitoring a current through the load using the current sensing subcircuit; and using the charge control circuit to modulate transfer of electrical energy in response to the monitored current through the load.

Additionally or alternatively, the load comprises a capacitor stack and an H-bridge configured to selectively couple the capacitor stack to an output of the implantable medical device, and the charge control circuit comprises a switch in series with the primary winding and the power source, such that: the step of monitoring a current through the load includes enabling the H-bridge circuit to issue a signal from the capacitor stack to the output, wherein the current is the current through the H-bridge; and the step of using the charge control circuit to modulate transfer of electrical energy comprises selectively opening and closing the switch.

Another illustrative and non-limiting example takes the form of an electronic circuit for controlling an output of an implantable medical device, the electronic circuit comprising: a transformer having a primary winding and at least one secondary winding; a power source selectively electrically coupled to the primary winding; a load coupled to the at least one secondary winding; a current sensing subcircuit coupled to the load; a charge control circuit configured to enable and disable current through the primary winding, wherein the charge control circuit takes a feedback signal from the current sensing subcircuit to control current through the primary winding, thereby controlling current output to the load via selective enabling and disabling of the power source to the primary winding.

Additionally or alternatively, the load comprises at least first and second capacitors each independently coupled to a secondary winding.

Additionally or alternatively, the charge control circuit is operable in a current controlling mode and defibrillation mode, wherein the current controlling mode is one in which the charge control circuit uses the feedback signal, and in the defibrillation mode, the charge control circuit does not use the feedback signal, to enable and disable current through the primary winding.

Additionally or alternatively, the charge control circuit comprises a control subcircuit that issues charger enable pulses to a switch in series with the primary winding and the power source to thereby transfer power from the battery to the transformer, wherein the charge control subcircuit is configured to modulate characteristics of the charger enable pulses in response to the feedback signal in the current controlling mode.

Additionally or alternatively, the charge control subcircuit is configured to adjust a width of one or more charger enable pulses. Additionally or alternatively, the charge control subcircuit is configured to adjust a period between successive ones of the charger enable pulses. Additionally or alternatively, the charge control subcircuit is configured to issue the charger enable pulses as a series of bursts of charger enable pulses, and, to modulate characteristics of the charger enable pulses, the charge control subcircuit is configured to omit at least one burst of the series of bursts. Additionally or alternatively, the charge control subcircuit is configured to issue the charger enable pulses as a series of bursts of charger enable pulses, and, to modulate characteristics of the charger enable pulses, the charge control subcircuit is configured to change how many pulses are in each of the series of bursts. Additionally or alternatively, the control subcircuit is configured to use a fixed pulse width to control the switch in the defibrillation mode. Additionally or alternatively, the control subcircuit is configured to monitor current through the primary winding to control the switch in the defibrillation mode.

Additionally or alternatively, the charge control circuit comprises a control subcircuit that issues charger enable pulses to a switch in series with the primary winding to thereby transfer energy from the battery to the transformer, wherein the charge control subcircuit is configured to modulate characteristics of the charger enable pulses in response to the feedback signal.

Yet another illustrative and non-limiting example takes the form of an implantable pacemaker-defibrillator comprising: a battery; a transformer having a primary winding and at least one secondary winding; a capacitor stack coupled to the at least one secondary winding; an H-bridge to deliver electrical signals from the capacitor stack to outputs of the defibrillator; a current sensing subcircuit coupled to the H-bridge; a charge control circuit configured to control electrical coupling of the primary winding to the power source; a system controller for the implantable defibrillator having control outputs to control operation of the H-Bridge and the charge control circuit; and a housing containing the battery, transformer, capacitor stack, H-bridge, current sensing subcircuit, charge control circuit and system controller; wherein the system controller is configured to selectively operate the charge control circuit in a pacing mode in which a feedback signal from the current sensing subcircuit is used to control current through the primary winding by operation of the charge control circuit.

Additionally or alternatively, the charge control circuit is configured to operate, in the pacing mode, by selective enabling and disabling of current through the primary winding in response to the feedback signal.

Additionally or alternatively, the capacitor stack comprises at least first and second capacitors each separately coupled to a secondary winding.

Additionally or alternatively, the system controller is configured to bypass the current sensing subcircuit to issue defibrillation signals.

Additionally or alternatively, the charge control circuit is operable in a defibrillation mode in which the charge control circuit ignores the feedback signal.

Additionally or alternatively, the charge control circuit is configured issue charger enable pulses that enable electrical coupling of the battery to the primary winding, and to modulate one or more characteristics of the charger enable pulses in response to the feedback signal in the current controlling mode.

Additionally or alternatively, the charge control subcircuit is configured to modulate one or more characteristics of the charger enable pulses by adjusting a width of one or more charger enable pulses. Additionally or alternatively, the charge control subcircuit is configured to modulate one or more characteristics of the charger enable pulses by adjusting a period between successive ones of the charger enable pulses.

Additionally or alternatively, the charge control subcircuit is configured to issue the charger enable pulses as a series of bursts of charger enable pulses, and, to modulate characteristics of the charger enable pulses, the charge control subcircuit is configured to omit at least one burst of the series of bursts. Additionally or alternatively, the charge control subcircuit is configured to issue the charger enable pulses as a series of bursts of charger enable pulses, and, to modulate characteristics of the charger enable pulses, the charge control subcircuit is configured to change how many pulses are in each of the series of bursts.

Additionally or alternatively, the device further comprises a lead, wherein the outputs of the pacemaker defibrillator include a first output coupled to a conductor in the lead, and a second output coupled to the housing, wherein at least a portion of the housing is conductive.

Another illustrative and non-limiting example takes the form of a method of operation in an implantable medical device comprising a transformer having a primary winding and at least one secondary winding, a power source selectively electrically coupled to the primary winding, a load coupled to the at least one secondary winding, a current sensing subcircuit coupled to the load, and a charge control circuit configured to enable and disable current through the primary winding, the method comprising: using the charge control circuit to cause the transformer to transfer electrical signal from the power source to the load; monitoring a current through the load using the current sensing subcircuit; and using the charge control circuit to modulate transfer of electrical energy in response to the monitored current through the load.

Additionally or alternatively, the load comprises a capacitor stack and an H-bridge configured to selectively couple the capacitor stack to an output of the implantable medical device, and the charge control circuit comprises a switch in series with the primary winding and the power source, such that: the step of monitoring a current through the load includes enabling the H-bridge circuit to issue a signal from the capacitor stack to the output, wherein the current is the current through the H-bridge; the step of using the charge control circuit to modulate transfer of electrical energy comprises selectively opening and closing the switch.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
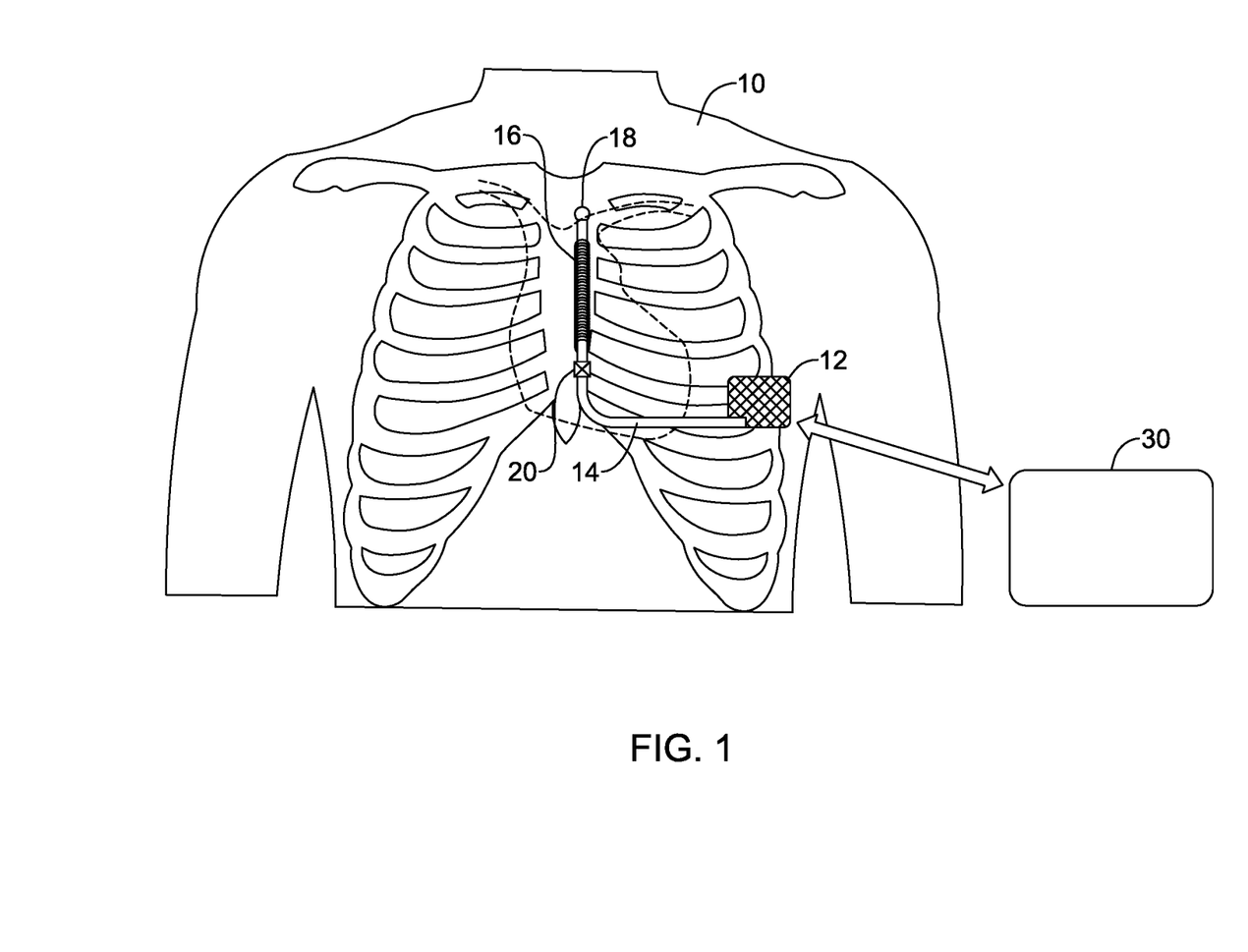
FIG. 1 shows an implantable stimulus system relative to the torso of a patient.

FIG. 1 shows an implantable stimulus system relative to the torso of a patient 10. In the example shown, an implantable canister 12 is placed near the left axilla, with a lead 14 extending medially therefrom. The lead 14 turns near the xiphoid to advance in a superior direction, toward the head generally parallel the sternum and over the heart. The lead 14 is shown illustratively as having a defibrillation coil electrode 16 and distal and proximal sense electrodes 18, 20. An external programmer 30 can wirelessly communicate with the canister 12 to provide therapy and sensing instructions to the system and to check various device status, history and diagnostic factors. The present invention is not limited to the specific lead 14 design shown, nor position of either the lead 14 or canister 12, and a variety of details and alternatives are disclosed in the patents and applications cited in the following paragraph, each of which may be used in various embodiments of the present invention.

The example of FIG. 1 shows the lead 14 placed over the ribs, in a subcutaneous position. Other subcutaneous positions may be used, such as described in US PG Pat. Pub. No. 20120029335, and U.S. Pat. Nos. 8,157,813, 7,149,575, 6,721,597, and 6,647,292, the disclosures of which are incorporated herein by reference. In other examples, the lead may be placed beneath the sternum in a substernal position, in the mediastinal space, as described in US PG Pat. Pub. No. 20170021159, and/or U.S. Pat. No. 10,471,267, the disclosure of which are incorporated herein by reference. In still other examples, the internal thoracic vasculature (including the internal thoracic vein or ITV) may be used for implantation as a final placement or as an avenue to the mediastinum, as described in US PG Pub. Nos. 20180133462, 20180036547, 20180036527, the disclosures of which are incorporated herein by reference. Such systems use sensing and therapy electrodes disposed in positions that neither contact nor enter the heart.

Approaches that use pacing electrodes that neither enter nor contact the cardiac tissue call for increased pacing amplitude when compared to transvenous, intracardiac or epicardial electrodes. Historically two separate output paths would be used for an implantable transvenous defibrillator having both pacing and defibrillation therapy capabilities, with a low voltage pacing therapy deliverable directly off of the battery stack or with a limited voltage boost, while a transformer-based circuit would be used to transfer power from the battery to a high voltage (HV) capacitor or capacitor stack for defibrillation purposes. However, with increased pacing amplitude needed for these newer, substernal, ITV, extracardiac or subcutaneous pacing configurations, the prior solutions become less usable. For example, with the SICD System™, three series batteries are used in the device, providing a nominal output voltage in the range of 9 to 9.5 volts, under light load; the pacing output of this system, used in the post-defibrillation shock context, delivers a 200 mA pacing output into a range of impedances from 25 to 200 ohms (assuming impedance measured during shock delivery), which means pacing can be delivered at up to 40 volts, more than four times the battery voltage. Pacing, when delivered, may be used for any of bradycardia support (chronic or post-defibrillation), as an anti-tachyarrhythmia pacing therapy, or for alleviation of heart failure systems, such as resynchronization therapy, without limitation.

Pacing is delivered at a relatively low duty cycle; a higher duty cycle, such as when inducing fibrillation for testing purposes (as is common at implant), can use a higher duty cycle, requiring still more DC:DC boosting capability. Induction testing is performed to demonstrate one or both of the sensing capability of an implanted system and its ability to convert ventricular fibrillation to a normal rhythm with therapeutic shock. In the realm of transvenous defibrillators, there is a trend away from universal induction testing. However, induction testing continues to be widely used, and in particular can be expected to be a continued practice with newer substernal, ITV, extracardiac and/or subcutaneous defibrillation systems.

Some proposals include adding a separate "pacing therapy" boost circuit and capacitor array to provide intermediate level power for pacing purposes. However, provision of multiple, separate circuits to provide the needed boosting increases complexity, cost, and space requirements, as well as complicating other factors such as reliability. A transformer-based circuit can be used to transfer very large amounts of power from a battery to a capacitor stack, and this technology is widely used in implantable defibrillators today to provide higher power cardioversion and/or defibrillation therapy outputs. Moreover, the commonly used output circuit for defibrillation therapy, which is called an H-bridge due to its shape, having first and second high side legs that meet at first and second load nodes with first and second low side legs, is already present in the device. New and better ways to facilitate multiple output levels, without overly complicating the apparatus, are desired.

While the development of the present invention may focus generally on some of the newer implant positions (subcutaneous, substernal, mediastinal or ITV), the present invention may also be used in more therapy systems with still older implantation positions, including epicardial or transvenous systems having leads and/or electrodes located in or on the heart.

Figure 2:
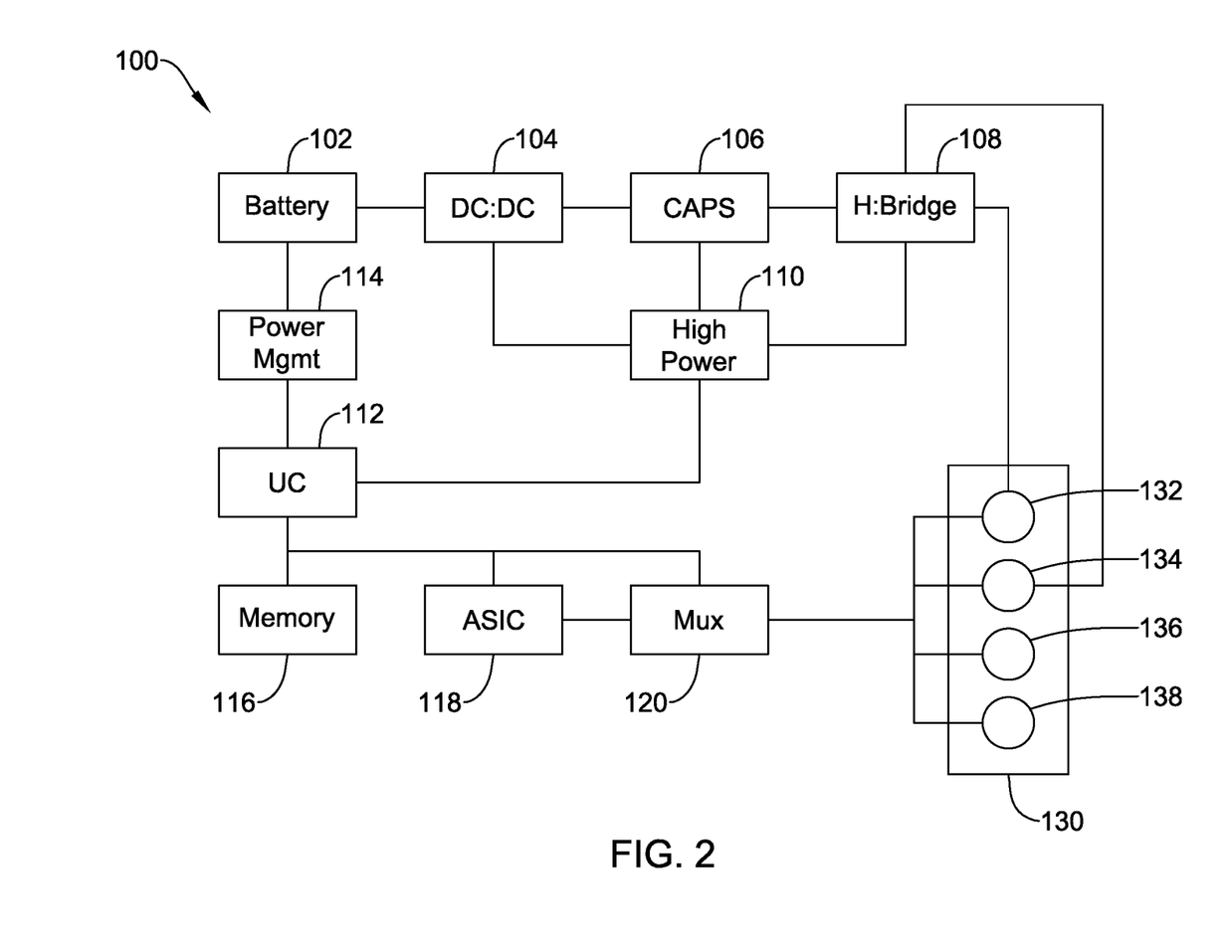
FIG. 2 shows an illustrative block diagram for an implantable stimulus system.

FIG. 2 shows an illustrative block diagram for an implantable stimulus system. The illustrative system 100 is powered by an internal battery 102, which may be of any suitable chemistry for an implantable medical device, such as any of various lithium chemistries (Lithium-Ion, LiMnO2, etc.). The battery 102 may comprise any suitable number of battery cells, such as 1, 2, 3, 4 or more cells. The battery 102 in the example is a non-rechargeable battery; in other examples a rechargeable battery may be used and, if so, a recharging circuit comprising, for example, an inductive coil that can be energized by an external coil may be used, such as described in U.S. Pat. No. 9,814,889 and/or as such systems are known for spinal cord stimulation such as in U.S. Pat. Nos. 8,548,590, 8,473,066 and/or 8,463,392, the disclosure of which are incorporated herein by reference.

The battery 102 can be used for high power therapy delivery by routing the battery output to a DC:DC converter 104 to charge a capacitor stack 106, with an H-Bridge used to issue therapy pulses via electrodes coupled to ports 132, 134. Optionally, in some examples, blocks 104, 106 and 108 reside on a high power hybrid (circuit board) 110 separate from lower power circuitry to reduce interference, among other benefits.

In some examples, a transformer is used as the DC:DC charging circuit, using a flyback transformer layout in which the battery output is directed to a primary coil of the transformer and one or more secondary coils each charge a capacitor of the capacitor stack 106. In operation, the charging sequence alternates between primary and secondary phases. During the primary phase, the transformer receives power from the battery 102, with current passing from the battery, through at least a switch and the transformer to ground. During the secondary phase, the switch is opened, causing an open circuit of the transformer primary coil, driving the energy stored in the transformer during the primary phase into the capacitor stack 106. Appropriately placed diodes can be used to manage current flow and ensure appropriate charging takes place. Switching between primary and secondary phases can be controlled via a timing schedule, or may occur in response to measured currents (measured directly or through voltage measurements) reaching upper or lower thresholds, or a combination of both, such as having a fixed interval primary phase and a current controlled secondary phase.

While several references herein are to a capacitor stack 106, having, for example, anywhere from 2-6 capacitors, or more, a single capacitor may be used if desired. The drawing indicates dedicated output or output ports 132, 134 which may be, for example, an output coupled to a conductive canister (or portion thereof) that contains the circuitry 100 and a port adapted to couple, electrically, to an electrode on a lead, wherein the port has an electrical connector that couples to output circuitry (such as an H-Bridge) of the system, and the lead has a proximal end connector with a corresponding electrical connector that is electrically coupled by a conductor through a lead body to the distal end of the lead, where one or more therapy electrodes are located. In other examples, two lead electrodes, or two housing electrodes, or more than two electrodes may be used for therapy delivery; additional switching circuitry may be used to direct therapy outputs as desired. In the illustrative example, lower power circuitry is (optionally) powered by a power management block 114 that provides regulated voltages off of the battery 102, such as, for example and without limitation, 1.8, 3.2, 5.1, or other voltages, which are typically reduced relative to the battery output to ensure stable voltages over the useful life of the device, during which the battery voltage typically degrades. Some examples may also include, for example, a 15 volt supply that can be generated by a switched capacitor voltage booster (assuming the battery 102 provides less than 15 volts). A plurality of such power supplies may be included to address various needs in the system, such as, for example and without limitation, providing a 5-volt supply to power a telemetry antenna while a 3.2 volt supply powers a microcontroller.

A microcontroller 112 may be provided for managing various device operations, with a memory 116 provided to store executable instructions as well as device history data, such as measured battery voltages and recorded cardiac data related to "episodes" in which therapy is delivered, as well as any other information or instructions used in the system. An application specific integrated circuit (ASIC) 118 is illustratively shown and, without intending to limit the invention any particular one of these items, may include circuits dedicated to particular tasks, such as an input ECG circuit that filters, amplifies and digitizes sensed signals. Other circuits on the ASIC may include dedicated beat detection circuitry, and/or dedicated morphology analysis circuitry such as a correlation analysis or wavelet comparison circuit. The ASIC 118 may comprise or be coupled to telemetry circuitry using, for example, Medradio, inductive telemetry, or Bluetooth (including Bluetooth Low Energy) communication circuitry. The power management block 114, or portions thereof, may be integrated into the ASIC 118 if desired.

A switching circuit is also shown as a multiplexor 120 for coupling to a plurality of inputs/outputs 130, shown as four input/output lines 132, 134, 136, 138; more or fewer input/output lines may be included. In some examples the switching circuitry is used to select one or more sensing vectors defined by pairs or groups of electrodes used for sensing purposes, such as disclosed, for example, in U.S. Pat. Nos. 8,825,157, 7,783,340, 8,200,341, and/or US PG Pat. Pub. Nos., 20170113053, 20170113050, 20170113040, and/or 20170112399, the disclosures of which are incorporated herein by reference.

Figure 3:
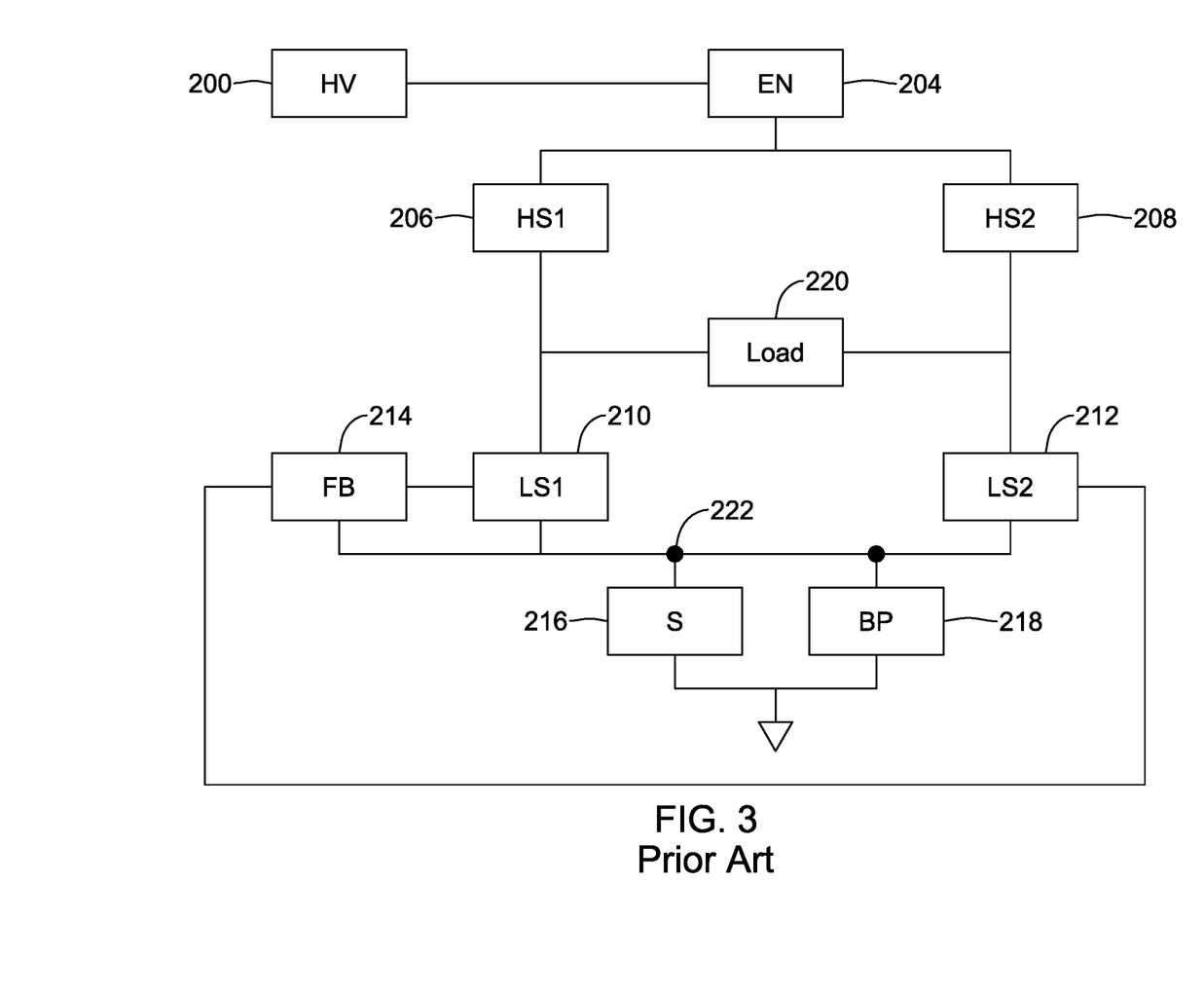
FIG. 3 shows a prior art output circuit.

FIG. 3 shows a prior art output circuit. The illustrative circuit delivers power from the HV Capacitors 200 to a load 220, which represents the patient. An enable switch 204 sit outside (above) the H-Bridge, which comprises two high side switches 206, 208 and two low side switches 210, 212. In this example, the low side switches 210, 212 can be used as ON/OFF switches during defibrillation, and can be used to control current during pacing and induction processes by the use of a feedback circuit 214. Between the H-Bridge and ground are a sense resistor 216 and a bypass switch 218.

To issue therapy, a combination of the enabling switch 204 and one high side and one low side switch are closed. In a first polarity output, switches 204, 206 and 212 are closed; to deliver output of the opposite polarity, switches 204, 208 and 210 are closed. During defibrillation therapy, the sense resistor 216 is bypassed by closing the bypass switch 218. Biphasic therapy can be issued by monitoring the HV capacitors 200 to determine when a threshold voltage for switching polarity is reached, such as 40, 50, 60, or 70% (or other value) drop in voltage.

For controlled current pacing and induction purposes, the bypass switch 218 is opened, forcing current through the sense resistor 216. The feedback circuit 214 obtains a sense signal from the sensing node 222 and provides a controlled enabling voltage to one of the low side switches 210, 212 (depending on which polarity of output is active) to keep the voltage at node 222 fixed to a predetermined value. For example, when the voltage at node 222 is lower than a target value, that means less than a target current is flowing through sense resistor 216, so the voltage provided to enable whichever of switches 210, 212 is being operated is increased until the voltage at node 222 reaches the target value.

To limit the amount of power that has to be absorbed by switches 210, 212, the HV capacitors 200 may be charged for pacing and induction to a voltage that is lower than that used for defibrillation, as, for example, by charging to a level that will enable current to reach the target value for the maximum allowable load impedance. For example, if the maximum allowable, or expected, load is 200 ohms and the current to be issued is 200 mA, then the HV capacitors 200 may be charged to a value that exceeds 40 volts plus some margin to account for losses due to the transistors and transmission lines in the circuit, as well as attenuation in the sense resistor 216, for example resulting in a voltage in the range of 45 to 100 volts, rather than several hundred or thousand-plus volts used for defibrillation.

A drain circuit for the HV capacitors 200 is omitted in the drawing, but may be understood as comprising one or two resistive branches. In a two-branch version, a passive drain branch having a large impedance (1 Mohm, for example) provides a slow drain on the HV capacitors to ensure that a large voltage is not held indefinitely, while a smaller resistor, sometimes called a dump resistor (10 kohm, for example), is provided in series with a switch to allow the HV capacitors 200 to be quickly drained to a reduced voltage if needed, for example, to allow pacing therapy output after a defibrillation shock if reduced HV cap voltage is desired during pacing relative to the residual voltage after defibrillation shock. Another context for using an active drain branch may be if a patient undergoing induction testing spontaneously converts to normal rhythm while the HV capacitors 200 are being charged, in which case is may be desirable to drain the HV capacitors 200 prior to the next induction attempt.

It should be understood that an H-bridge, as that term is used, may have more than two high and/or low side legs to allow the use of more than one output vector, if desired. References herein to first and second high and/or low side legs of an H-bridge should be understood as not limiting to just two such legs.

In this circuit, because the low side switches 210, 212 are used to control current flow, they have to absorb a significant amount of power in the controlled current mode, and typically relatively large IGBT devices are used. Also in this circuit, the high side switches 206, 208, and the enable switch 204, are subject to a level shift during therapy output, as the load raises the emitter voltage on each to, practically speaking, the voltage on the HV capacitors 200. Therefore an isolation circuit element, such as a transformer or optical isolator, is typically used to provide the control signal to each switch 204, 206, 208, reliant on a low voltage input. The use of larger IGBT elements and the isolation elements increases cost and size of the circuit, and the isolation circuits may also add to the potential for quality issues, as optical isolators can be subject to thermal issues during manufacturing. Alternatives are desired.

Figure 4:
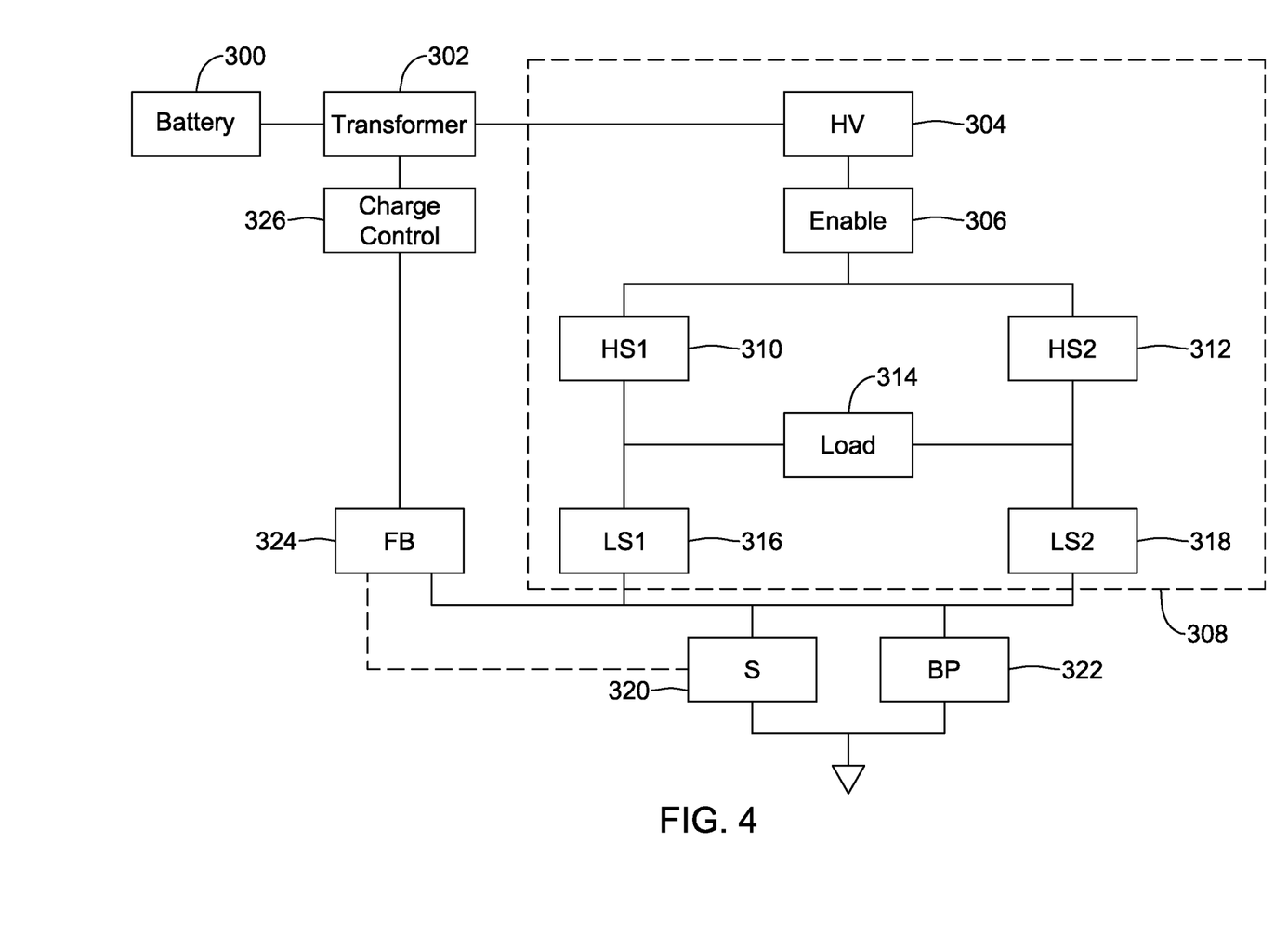
FIG. 4 shows a new output circuit design in block form.

FIG. 4 shows a new output circuit design in block form. The circuit receives power from a power source shown as a battery 300 at a transformer 302, which provides an output to a load 308 shown here as including an HV capacitor stack 304. The HV capacitor stack 304 is coupled via an enable switch 306 to an output circuit shown as including an H-Bridge having high side switches 310, 312 and low side switches 316, 318 that connect to output ports adapted to couple to a patient load 314. The H-bridge is coupled to ground via a current sense block 320 placed in parallel with a bypass switch 322. A feedback circuit 324 takes a feedback signal from the current sense block 320 as a feedback signal, which is provided to a charge control block 326.

In some examples, the current sense block 320, with or without the bypass switch 322, and the feedback circuit 324 may be described as a current monitoring subcircuit. A current monitoring subcircuit may further comprise, for example, a comparator or an analog-to-digital convertor as the feedback circuit 324. A comparator may be used, for example, in the feedback circuit 324 to compare the voltage across a sense resistor (serving as current sense block 320), to a predetermined voltage, or a controllable voltage, to provide an indication of whether the voltage through the sense resistor (which is directly proportional to the current therethrough) is above or below a target or threshold that the predetermined or controllable voltage is indicative of. An analog to digital convertor, if used, provides a measurement output in digital form telling the system controller what voltage has been measured; again, the voltage through the sense resistor would be directly proportional to the current, and knowing the resistance value of the sense resistor, simple division allows the current to be calculated. Thus, for example and without limitation, if a comparator is used, and a 50 ohm resistor is used as a sense resistor, to obtain a 100 milliamp current, the predetermined or controllable voltage may be 5 volts. In another example, an inductive current measuring apparatus is used as the current sense block 320 using, for example, a Hall effect device or flux gate sensor to sense current flow, with or without a bypass switch 322, in which case the feedback circuit 324 may comprise suitable driver and control circuitry for the Hall effect device or flux gate sensor, as the case may be and in accordance with known designs in the field.

Another alternative configuration of the circuit may include the use of one or more diodes in place of the bypass switch 322. A forward biased diode/rectifier, or reverse biased Zener diode, may be used in place of a switch at 322, as long as the current sense block 324 has sufficient current carrying capacity to accommodate however much current would flow during defibrillation due to the forward voltage of the diode/rectifier (or reverse breakdown voltage if a Zener diode is used).

The charge control block 326 receives a signal from the feedback circuit 324 in any of several forms. In one example, the signal received by the charge control block 326 is either high or low, indicating whether the current through the H-Bridge is above or below a target. In another example, the signal received by the charge control block 326 may be a measure of current itself, and the charge control block 326 determines whether the current is above, at or below a target. The charge control block 326 in turn is coupled to the transformer 302 and controls power transfer from the power source (battery 300, with or without fuse and/or coupling capacitor(s) associated therewith) to the transformer and load 308. In some examples, the charge control block 326 is coupled to a primary winding of the transformer 302 to enable or disable current flow from the power source through the primary winding, such as in an ON/OFF fashion. It should be noted that "primary winding" as used herein, is not necessarily the structural or labeled "primary winding" of the transformer 302, but is instead a reference to the winding of the transformer 302 that receives current from the power source or battery 300.

In use, the circuit can provide at least controlled current output as follows. When a controlled current output is desired, the transformer 302 is enabled by the charge control circuit 326 to provide power to the load 308 from the battery 300. As current is issued in the load, it is measured at the current sense block 320 and feedback circuit 324, as explained above. The charge control circuit 326 then modulates power delivered to the transformer from the battery to keep the delivered current in a desired range. In some examples, at controlled current output turn-on, it may take one or more cycles for the circuit to settle to a controlled current or steady state operation; such onset conditions are still considered controlled current operation as that term is used herein.

In another use example, the load 308 is viewed with greater detail. Here, at turn-on, the charge control circuit 326 initially enabled power transfer from the power source or battery 300 via transformer 302 to the HV capacitor or capacitor stack 304. When the HV capacitor or capacitor stack 304 reaches a desired initial voltage, power transfer stops. The enable switch 306 and H-Bridge are used to deliver current to the patient load 314, with the current sense circuit 320 and feedback circuit 324 providing a feedback signal to the charge control circuit 326, which can allow more or less power to be transferred with each output pulse delivery, again settling over time to a steady state. In some examples, the charge control circuit 326 provides a pulse width modulated signal to the transformer that sets a transformer duty cycle; if output current is above the target, the pulse width modulated signal is modified to reduce the duty cycle; if the output current is below the target, the pulse width modulated signal is modified to increase the duty cycle; finally, if the output current is at the target, the pulse width modulated signal is kept as-is. In other examples, the amount of charge issued with each output pulse is small enough that the HV capacitor or capacitor stack 304 does not need additional energy input with each pulse, and the charge control circuit 326 only enables the transformer 302 when current delivered starts to drop below the target.

A variety of different approaches may be used to manage or modulate the energy delivered to the HV capacitor or capacitor stack 304 from the transformer 302. In some examples, burst charging is used, in which a set of pulses are delivered at a first period in a "burst" separated from a subsequent burst by a second period that is longer than the first period. To use burst charging, the charge control 326 enables the transformer primary winding to receive energy from the battery 300 for periods associated with each pulse of the burst, and otherwise disables the transformer primary winding from receiving energy from the battery 300. For a burst charging regimen, the quantity of pulses in each burst may be modified, by increasing the quantity to up-modulate the power transfer, or decreasing the quantity to down-modulate the power transfer. In another example, the period between bursts can be modified by extending or reducing the period to down-modulate, or up modulate, respectively, the power transfer. In another example, a cycle may be dropped by disabling a burst entirely, referred to as a drop cycle within a burst charging method. These examples of burst charging modulation are operable to increase or reduce the charging duty cycle, which can be defined for purposes herein as the ratio of the amount of time the transformer primary winding receives energy from the battery, divided by the total time of the charging operation.

Burst charging may be viewed as a form of schedule-controlled charging. In other examples, current controlled charging can be used. With current controlled charging, currents through the primary or secondary side of the transformer can be monitored to determine when switching events occur. For example, a charger control circuit 326 may enable the primary winding to receive power from the battery 300 until current through the primary winding reaches a threshold, and then disable the primary winding to force current out through the secondary winding(s); current is then monitored in the secondary winding(s) until it drops below a threshold, at which time the charger control circuit 326 enables the primary winding to receive power again. With purely current controlled charging, the peak current threshold for the primary winding can be reduced to down-modulate charging, or increased to up-modulate charging (so long as the current remains below an upper limit to avoid saturating the core of the transformer 302). In another approach, the secondary winding current threshold can be reduced to down-modulate charging, or increased to up-modulate charging. In a mixed example, the primary winding is controlled in a scheduled manner, and the secondary winding is current-controlled, such that charging occurs by enabling the primary winding for a set period of time, then disabling the primary winding to force current out through the secondary winding, and keeping the primary winding disabled until the secondary winding current drops below a threshold. In the mixed example, reducing the time period for enabling the primary winding can down-modulate charging, while increasing the time period for enabling the primary winding will up-modulate charging. Further in the mixed example, the threshold secondary winding current used to re-enable the primary winding can be increased to up-modulate charging, or decreased to down-modulate charging. With the current-controlled or mixed approaches, the charger control circuit 326 may also down-modulate charging by enforcing pauses between re-enabling energy transfer to the primary winding from the battery 300.

In still other examples, the charge control circuit 326 may be configured to receive timing signals related to the H-bridge operation. In an example, the transfer of energy from the battery to the transformer 302, and then from the transformer to the HV capacitor or capacitor stack 304 may be prevented during therapy to avoid voltage spikes affecting the therapy output. This function is optional, however, as it may be recognized that the HV capacitor or capacitor stack can buffer the output from spikes occurring as the transformer operates during charging.

The system may be configured to provide the output "constant current" within engineering boundaries, such as plus/minus a set percentage or quantity, for example. Some examples may allow variation in the range of about 0.1 to 20 milliamps, or 1% to 20% variation, depending on the system configuration. With "constant current" allowed to vary within such limits, the periodic or intermittent power transfer via the transformer can used in a differential and/or proportional feedback loop.

As noted above, the system may include active drain circuit paths from the HV capacitor or capacitor stack 304 to ground; if at initial startup the current output is above range, the active drain circuitry may be used to reduce voltage on the HV capacitor or capacitor stack 304 to shorten the time to steady state condition and avoid overcurrent through the load 308 and/or to the patient load 314.

In some examples, the voltage on the HV capacitor or capacitor stack 304 may be monitored and recorded during operation in order to set target initial parameters for subsequent therapy. For example, if the system is configured for providing anti-tachyarrhythmia pacing (ATP) in a constant current mode, the pacing operation may be called only occasionally such as a few times a year. When delivering a first ATP therapy, the initial charging of the HV capacitor or capacitor stack 304 may be set to a default level, and steady state parameters observed may be recorded so that a later ATP therapy can be use the measured HV capacitor or capacitor stack voltage during steady state as the initial charging level.

This same circuit may also be used to deliver defibrillation therapy by operating the charge control circuit 326 in a separate defibrillation mode, in which charging of the HV capacitor or capacitor stack 304 is performed without use of any feedback signal from the low side of the H-bridge. Such charging operation may rely on measuring currents through primary and secondary windings, and/or may be performed according to a schedule, and/or using a hybrid of current-measured and scheduled primary and secondary phases, as desired. During therapy output, if the current sensing block 320 is a resistor, the bypass switch 322 may be closed to allow maximum current flow through the patient load 314, if desired.

Figure 5:
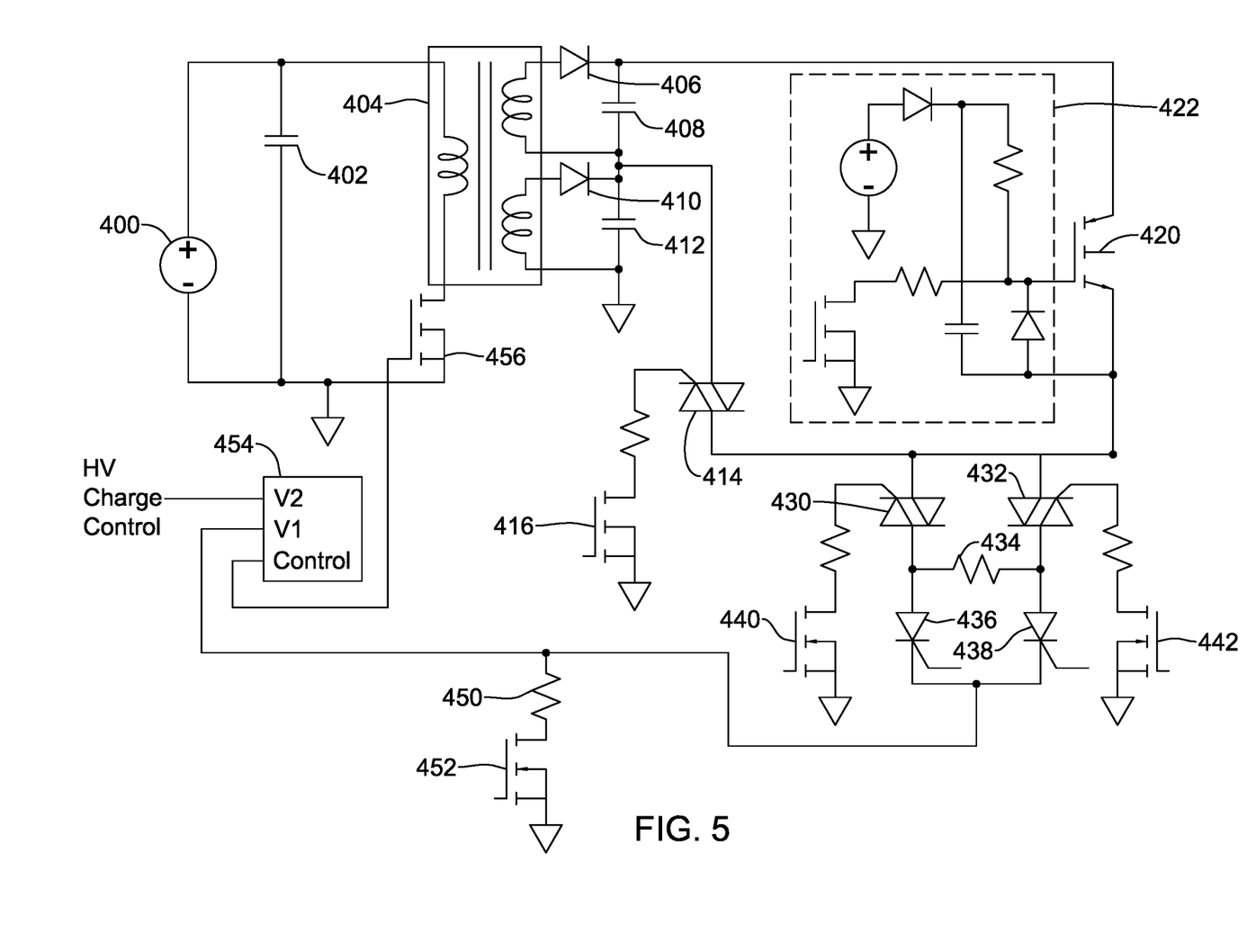
FIG. 5 shows a new circuit for current control through a transformer.

FIG. 5 shows a new circuit for current control using the transformer. An illustrative schematic is shown with specific circuit elements; other specific elements may be used in various places equivalently with those shown, and the specific example shown is intended to be non-limiting; other schematics may be used to realize a circuit as shown in either of FIG. 4 or 6, for example. A power source comprises a battery 400 and coupling capacitor 402. The coupling capacitor 402 aids in reducing voltage ripple to other parts of the device when the transformer 404 is enabled.

The transformer 404 is shown as having one primary coil and two secondary coils; more or fewer secondary coils may be provided. The secondary coils are coupled with diodes 406, 410 to first and second HV capacitors 408, 412 that are stacked relative to ground. Although not required, the configuration shown separates a pacing output that routes from a subset (shown as only one, but any number could be used) of the capacitors 412 through a pace-enable switch 414, shown as a TRIAC device, having driver 416 to the H-bridge. A defibrillation output path receives power from both capacitors 408, 412 stacked, goes to a defibrillation enable switch 420, shown as an IGBT, having a driver 422 (shown as a bootstrap driver) to the H-bridge.

In another example, a single capacitor may be used as the HV capacitor stack, but the transformer may include a secondary winding having one or more taps. In this example, when higher energy therapy, such as cardioversion or defibrillation, is needed, the full secondary winding is used to charge the HV capacitor stack, and when a lower energy output, such as pacing or induction signals, is needed, only a portion of the secondary winding is used to charge the capacitor by using appropriately placed switching to go from using the full secondary winding to only using a portion thereof.

Figure 6:
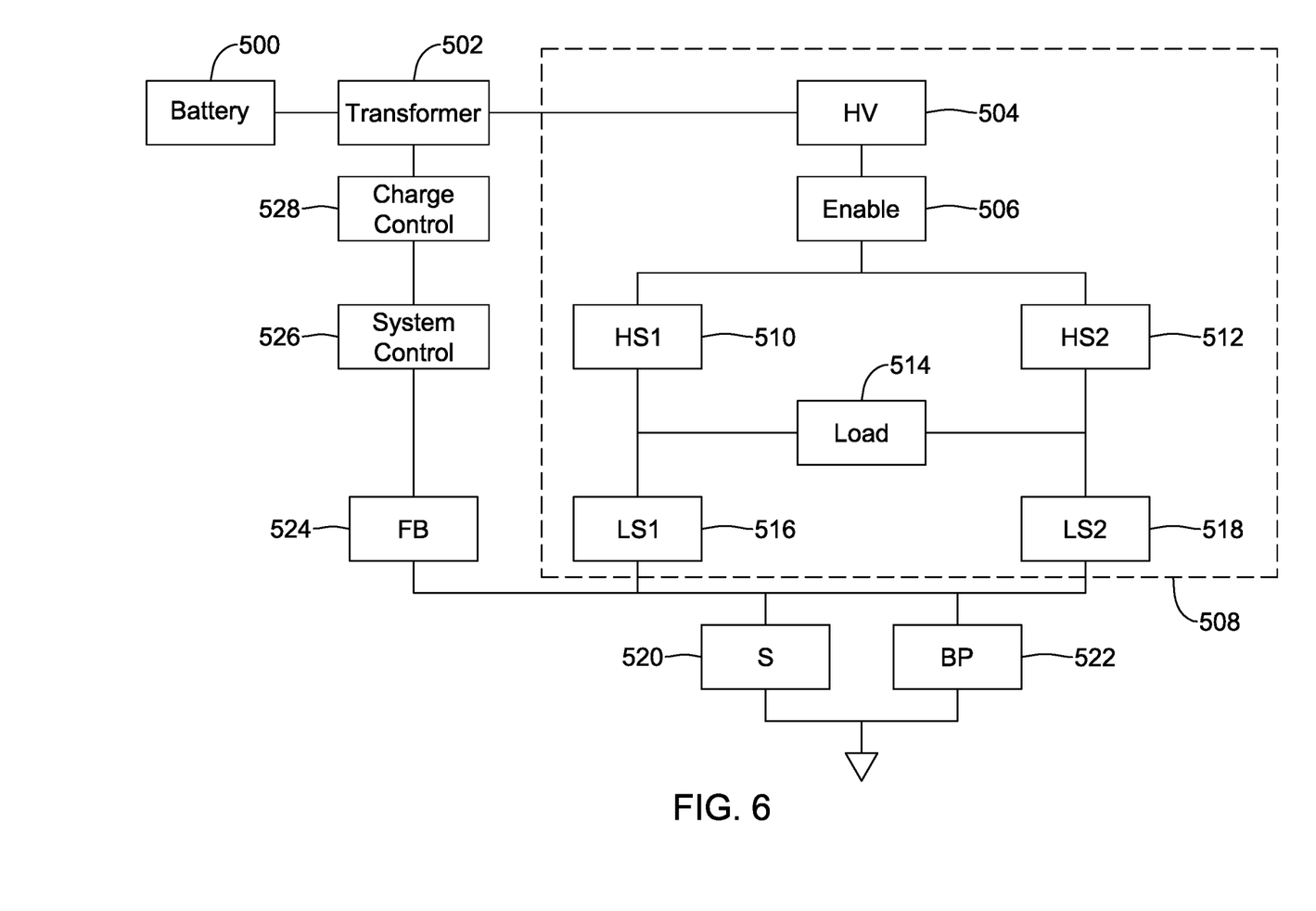
FIG. 6 shows another new output circuit design in block form.

The H-bridge is shown with high side switches 430, 432, shown as TRIAC devices, each having an enable circuit 440, 442, and low side switches 436, 438, shown as silicon controlled rectifiers. It may be noted that the current sense circuit is shown as a resistor 450 in series with a field effect transistor 452; in use, when pacing is delivered via switch 414 and the H-bridge, none of the control transistors can be turned off, so the switch at 452 is used to terminate the pace pulse by opening, causing current flow to drop below the minimum needed to keep the switches in the H-bridge and TRIAC 414 on, serving to end the pace (or induction) pulse. The circuit shown in FIG. 5 omits a bypass switch, though such can readily be included in parallel with the elements of the current sense circuit at 450, 452, as shown in FIGS. 3, 4 and 6.

The specific choices of transistor/switch type, and associated enable/disable circuitry, are not intended to be limiting to the overall disclosure. It may be noted generally that the choices shown may in some examples be advantageous in that the number of IGBT devices has been reduced to a single defibrillation enable IGBT at switch 420. Other switches in the enable and H-Bridge circuitry can be switches that, once closed, remain closed until current drops below a lower limit. The single IGBT 420, in this example, is used during defibrillation in order to open while the capacitor stack remains at least partly charged to truncate one or more phases of a defibrillation therapy. In another example, the current output for pacing purposes may be routed through switch 420, using the full capacitor stack, and the circuit patch using only half the capacitor stack through switch 414 (and associated enable circuit 416) can be omitted, optionally.

The current sensing resistor 450 provides a voltage signal proportional to delivered current to the charge control circuit 454, which compares the feedback signal received to a target voltage and provides a control signal to an enable switch 456 coupled to the primary side coil of the transformer 404. In this example, the HV charge control circuit 454 is described as performing as a comparator. If desired, additional switching functionality may be built in to limit the output control circuit to only allow it to be High when switch 452 is open, that is, when no constant current pace or induction output is active. In other examples, the charger may be operated during pace pulse and/or induction pulse delivery.

In other examples, the HV charge control circuit 454 may be provided by a system controller, such as a microcontroller, that tracks other operations as well. More typically, however, the HV charge control circuit 454 performs most operations on its own and receives supervisory control signals from the microcontroller, which may remain in a low power state except in response to interrupts or other wake-ups.

When a controlled current output is desired, an initial voltage is provided on the capacitors 408, 412, and the switch at 414 (or 420) is closed by a control signal from 416, along with a desired combination of the H-bridge switches to provide the desired polarity output to the patient load 434 (that is, either switches 430 and 438 are closed, or switches 432 and 436 are closed), allowing current to flow through the H-bridge and patient load 434 to the sense resistor 450, which provides a voltage feedback to the control at 454. When the current is below a target, switch 456 is operated to conduct additional power onto the HV capacitors 408, 412. If the current is above the target, an active drain circuit (not shown) may be used to reduce the voltage on the capacitors 408, 412, if desired. When the constant current pulse has been delivered for the desired pulse width, switch 452 is opened to truncate the pulse output, allowing the other switches in the output circuit to close.

When the transformer 404 conducts power to the HV capacitor stack 408, 412, in this example, the design is configured to deliver current either equally to the two capacitors or, if one capacitor holds a higher voltage than the other, only to the capacitor having the lower voltage. As a result, in effect, the capacitors 408, 412 are being charged in parallel (at least in the AC sense), and the configuration prevents overcharging of capacitor 408 during constant current operation in which power is only transferred out of capacitor 412 to the H-bridge.

FIG. 6 shows another new output circuit design in block form. The circuit receives power from a power source shown as a battery 500 at a transformer 502, which provides an output to a load 508 shown here as including an HV capacitor stack 504. The HV capacitor stack 504 is coupled via an enable switch 506 to an H-Bridge including high side switches 510, 512 and low side switches 516, 518 that connect to a patient load 514. The H-bridge is coupled to ground via a current sense block 520 placed in parallel with a bypass switch 522. A feedback circuit 524 takes a feedback signal from the current sense block 520 as a feedback signal, which is provided to a system controller 526 which in turn provides control inputs to a charge control block 528.

In some examples, the current sense block 520, with or without the bypass switch 522, and the feedback circuit 524 may be described as a current monitoring subcircuit. A current monitoring subcircuit may further comprise, for example, a comparator or an analog-to-digital convertor as the feedback circuit 524. A comparator may be used, for example, in the feedback circuit 524 to compare the voltage across a sense resistor (serving as current sense block 520), to a predetermined voltage, or a controllable voltage, to provide an indication of whether the voltage through the sense resistor (which is directly proportional to the current therethrough) is above or below a target or threshold that the predetermined or controllable voltage is indicative of. An analog to digital convertor, if used, provides a measurement output in digital form telling the system controller what voltage has been measured; again, the voltage through the sense resistor would be directly proportional to the current, and knowing the resistance value of the sense resistor, simple division allows the current to be calculated. Thus, for example and without limitation, if a comparator is used, and a 50 ohm resistor is used as a sense resistor, to obtain a 100 milliamp current, the predetermined or controllable voltage may be 5 volts. In another example, an inductive current measuring apparatus is used as the current sense block 520 using, for example, a Hall effect device or flux gate sensor to sense current flow, with or without a bypass switch 522, in which case the feedback circuit 524 may comprise suitable driver and control circuitry for the Hall effect device or flux gate sensor, as the case may be and in accordance with known designs in the field.

The system controller 526 receives a signal from the feedback circuit 524 in any of several forms. In one example, the signal received by the system controller 526 is either high or low, indicating whether the current through the H-Bridge is above or below a target. In another example, the signal received by the system controller 526 may be a measure of current itself, and the system controller 526 determines whether the current is above, at or below a target. The system controller 526 provides control signals to a charge control block 528 that controls power transfer from the power source (battery 500, with or without fuse and/or coupling capacitor(s) associated therewith) to the transformer 502 and load 508. In some examples, the charge control block 528 is coupled to a primary winding of the transformer 502 to enable or disable current flow from the power source 500 through the primary winding, such as in an ON/OFF fashion. It should be noted that "primary winding" as used herein, is not necessarily the structural or labeled "primary winding" of the transformer 502, but is instead a reference to the winding of the transformer 502 that receives current from the power source or battery 500.

In use, the circuit can provide at least controlled current output as follows. When a controlled current output is desired, the transformer 502 is enabled by the charge control circuit 528, which is in turn responsive to a signal from the system controller 526, to provide power to the load 508 from the battery 500. As current is delivered to the load, it is measured at the current sense block 520 and feedback circuit 524, as explained above.

The system controller 526 then uses the charge control circuit 528 to modulate power delivered to the transformer 502 from the battery 500 to keep the delivered current in a desired range. In some examples, at controlled current output turn-on, it may take one or more cycles for the circuit to settle to a controlled current or steady state operation; such onset conditions are still considered controlled current operation as that term is used herein. While the operation is described here as relying directly on the system controller 526, in some examples, the overall system architecture is as shown above in FIG. 2, with a microcontroller 112 that is kept in a low power state most of the time, and an ASIC 116 instead provides control signals to the circuit. In some examples, most elements of FIG. 6, including the transformer 502, charge control 528, output circuitry 508, sense circuit 520, bypass switch 522, and feedback circuit 524 are provided on a high power hybrid or circuit board, with a high power hybrid control subcircuit including the charge control 528 and feedback 524 included therein, which would in turn be linked to the ASIC 116 (FIG. 2) located on a separate circuit board (sometimes called a low power hybrid) for ongoing operation, with overall supervisory control provided by the microcontroller 112 (FIG. 2). Other architectures may be used as desired. As a result, in this example and others herein, the system controller can provide either active control, or may be passive, during the operations and methods described.

In another use example, the load 508 is viewed with greater detail. Here, at turn-on, the system controller 526 uses charge control circuit 528 to initially enable power transfer from the power source or battery 500 via transformer 502 to the HV capacitor stack 504. When the HV capacitor stack 504 reaches a desired initial voltage, the system controller 526 uses charge control circuit 528 to stop power transfer. The enable switch 506 and H-Bridge are used to deliver current to the patient load 514, with the current sense circuit 520 and feedback circuit 524 providing a feedback signal to the system controller 526, which can allow more or less power to be transferred with each output pulse delivery, again settling over time to a steady state. In some examples, the charge control circuit 528 provides a pulse width modulated signal to the transformer 502 that sets a transformer duty cycle; if output current is above the target, the system controller 526 uses the charge control circuit 528 to reduce the duty cycle; if the output current is below the target, the system controller 526 uses the charge control circuit 528 to increase the duty cycle; finally, if the output current is at the target, the pulse width modulated signal is kept as-is. In other examples, the amount of charge issued with each output pulse is small enough that the HV capacitor or capacitor stack 304 does not need additional energy input with each pulse, and the system controller 527 uses the charge control circuit 528 to enable the transformer 502 only when current delivered starts to drop below the target.

The system may be configured to provide the output "constant current" within engineering boundaries, such as plus/minus a set percentage or quantity, for example. Some examples may variation in the range of about 0.1 to 20 milliamps, or 1% to 20% variation, depending on the system configuration. With "constant current" allowed to vary within such limits, the periodic or intermittent power transfer via the transformer can used in a differential or proportional feedback loop.

As noted above, the system may include active drain circuit paths from the HV capacitor or capacitor stack 504 to ground; if at initial startup the current output is above range, the active drain circuitry may be used to reduce voltage on the HV capacitor or capacitor stack 504 to shorten the time to steady state condition and avoid overcurrent through the load 508 and/or to the patient load 514.

In some examples, the voltage on the HV capacitor or capacitor stack 504 may be monitored and recorded during operation in order to set target initial parameters for subsequent therapy. For example, if the system is configured for providing anti-tachyarrhythmia pacing (ATP) in a constant current mode, the pacing operation may be called only occasionally such as a few times a year. When delivering a first ATP therapy, the initial charging of the HV capacitor or capacitor stack 504 may be set to a default level, and steady state parameters observed may be recorded so that a later ATP therapy can be use the measured HV capacitor or capacitor stack voltage during steady state as the initial charging level. Any such recording may be scaled using desired current levels, as for example may be used if the constant current output is configurable within a range of currents.

This same circuit may also be used to deliver defibrillation therapy by operating the charge control circuit 528 in a separate defibrillation mode when called for by the system control 526. In defibrillation mode, charging of the HV capacitor or capacitor stack 504 is performed without use of any feedback signal from the low side of the H-bridge.

Such charging operation may rely on measuring currents through primary and secondary windings, and/or may be performed according to a schedule, and/or using a hybrid of current-measured and scheduled primary and secondary phases, as desired. During therapy output, if the current sensing block 520 is a resistor, the bypass switch 522 may be closed to allow maximum current flow through the patient load 514, if desired.

Therapy decision making may include any of a variety of algorithms known in the art. In general, referring back to FIG. 1, the microcontroller 112 and associated memory and ASIC components may be adapted to receive electrical signals from the electrodes which are amplified and filtered to provide an input ECG signal. The input ECG signal can be compared to a time-varying threshold to detect heart beats, such as by detecting R-waves or QRS complexes in the cardiac signal. Such detections can be confirmed by analyzing for double detection and noise using known methods. The time elapsing between detected heart beats is recorded in order to calculate cardiac rate, which can be categorized suitable for a given system. For example, a pacemaker defibrillator may have a timeout period applied to detect long pauses between beats, indicating pacing should be delivered for bradycardia conditions. An adaptive pacemaker may use an input from, for example, a temperature sensor or motion detector, to adjust the timeout period to account for patient activity, allowing the paced heart rate to increase or decrease depending on patient activity. A defibrillator or tachyarrhythmia therapy system may also classify ventricular tachyarrhythmia (VT) and ventricular fibrillation (VF) rates, such as considering rates between 180 and 220 beats per minute (BPM) as VT, and rates above 220 BPM as VF (other rate threshold may be used, and the thresholds may be configurable by a physician or at a physician's request/order). VT rates may be used to trigger ATP, for systems that provide ATP and in which ATP is enabled. VF rates may trigger additional analysis for shock delivery, such as using an X/Y counter to determine how many beats (X) of a set of Y beats are deemed to indicate VF using, for example, shape analysis (morphology). Illustrative shape analysis techniques can include the use of correlation waveform analysis, in which a stored template of a "normal" beat electrical signature is compared to detected beats; low correlation may be deemed indicative of VF; detected beats may be compared one to another as well to differentiate VT from VF and/or to differentiate sinus tachycardia (resulting from exercise, for example) from VT and VF. Wavelet transformation analysis may also be used to analyze shape, as well as the width of beats. When VF is identified, preparations for defibrillation therapy can be commenced, including charging the capacitor stack to a defibrillation energy level (typically 30 Joules or more, and higher still if a subcutaneous-only system is used, where 60 Joules or more may be used).

In an example, a beat detection routine may be as described in U.S. Pat. No. 8,565,878, with cardiac signal analysis for overdetection performed as in U.S. Pat. No. 8,160,686. Arrhythmia discrimination may be performed using methods described in U.S. Pat. Nos. 6,754,528 and/or 7,330,757. With beats analyzed for arrhythmia, the overall rhythm may be assessed using methods as in US Patent Application Pub. No. 2006/01467503, and defibrillation therapy can be delivered when all requirements for defibrillation therapy have been met, meaning that sufficient arrhythmic beats are detected in a persistent manner allowing positive confirmation of treatable arrhythmia. The disclosures of each of these patents and patent applications are incorporated herein by reference for at least the purposes identified for each. However, other methods may be used at each step, if desired, and the invention is not limited to use with these particular algorithms.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable pacemaker-defibrillator comprising:
a battery;
a transformer having a primary winding and at least one secondary winding;
a capacitor stack coupled to the at least one secondary winding;
an H-bridge to deliver electrical signals from the capacitor stack to outputs of the defibrillator, the H-bridge including first and second high side switches and first and second low side switches;
a current sensing subcircuit coupled to the H-bridge and positioned between the first and second low side switches and a reference or ground node to measure current flow out of the first and second low side nodes;
a charge control circuit configured to control electrical coupling of the primary winding to the battery;
a system controller for the implantable defibrillator having control outputs to control operation of the H-Bridge and the charge control circuit; and
a housing containing the battery, transformer, capacitor stack, H-bridge, current sensing subcircuit, charge control circuit and system controller;
wherein the system controller is configured to selectively operate the charge control circuit in a pacing mode in which a feedback signal from the current sensing subcircuit is used to control current through the primary winding by operation of the charge control circuit;
wherein the at least one secondary winding includes a first secondary winding and a second secondary winding, the capacitor stack includes at least a first capacitor and a second capacitor, the first capacitor is coupled to the first secondary winding, and the second capacitor is coupled to the second secondary winding;
the implantable pacemaker-defibrillator further comprising a defibrillation enable switch coupling the capacitor stack to the H-bridge, and a pacing enable switch coupling only one of the first capacitor and the second capacitor to the H-bridge, and
wherein the system controller is configured to:
operate in the pacing mode by selectively closing the pacing enable switch and not the defibrillation enable switch, and
to operate in a defibrillation mode by selectively closing the defibrillation enable switch and not the pacing enable switch.

2. The implantable pacemaker-defibrillator of claim 1 wherein the charge control circuit is configured to operate, in the pacing mode, by selective enabling and disabling of current through the primary winding in response to the feedback signal.

3. The implantable pacemaker-defibrillator of claim 1 in which the system controller is configured to bypass the current sensing subcircuit to issue defibrillation signals.

4. The implantable pacemaker-defibrillator of claim 1 wherein the charge control circuit is operable in a defibrillation mode in which the charge control circuit ignores the feedback signal.

5. The implantable pacemaker-defibrillator of claim 1 wherein the charge control circuit is configured to issue charger enable pulses that enable electrical coupling of the battery to the primary winding, and to modulate one or more characteristics of the charger enable pulses in response to the feedback signal in the current controlling mode.

6. The implantable pacemaker-defibrillator of claim 5 wherein the charge control subcircuit is configured to modulate one or more characteristics of the charger enable pulses by adjusting a period between successive ones of the charger enable pulses.

7. The implantable pacemaker-defibrillator of claim 5 wherein the charge control subcircuit is configured to issue the charger enable pulses as a series of bursts of charger enable pulses, and, to modulate characteristics of the charger enable pulses, the charge control subcircuit is configured to omit at least one burst of the series of bursts.

8. The implantable pacemaker-defibrillator of claim 5 wherein the charge control subcircuit is configured to issue the charger enable pulses as a series of bursts of charger enable pulses, and, to modulate characteristics of the charger enable pulses, the charge control subcircuit is configured to change how many pulses are in each of the series of bursts.

9. The implantable pacemaker-defibrillator of claim 1 further comprising a lead, wherein the outputs of the pacemaker defibrillator include a first output coupled to a conductor in the lead, and a second output coupled to the housing, wherein at least a portion of the housing is conductive.

10. The implantable pacemaker-defibrillator of claim 5 wherein the charge control subcircuit is configured to modulate one or more characteristics of the charger enable pulses by adjusting a width of one or more charger enable pulses.

* * * * *